United States Patent [19]

Kosa

[11] Patent Number: 4,695,697
[45] Date of Patent: Sep. 22, 1987

[54] FIBER TIP MONITORING AND PROTECTION ASSEMBLY

[75] Inventor: Nadhir B. Kosa, Minneapolis, Minn.

[73] Assignee: GV Medical, Inc., Minneapolis, Minn.

[21] Appl. No.: 808,737

[22] Filed: Dec. 13, 1985

[51] Int. Cl.⁴ ............................................. B23K 26/02
[52] U.S. Cl. .................. 219/121 LZ; 219/121 LB; 219/121 LR; 350/96.26
[58] Field of Search .... 219/121 LA, 121 L, 121 LM, 219/121 LZ, 121 LQ, 121 LR, 121 LB; 350/96.26, 96.25

[56] References Cited

U.S. PATENT DOCUMENTS

| | | | |
|---|---|---|---|
| 4,267,844 | 5/1981 | Yamanishi | 128/633 |
| 4,273,109 | 6/1981 | Enderby | 350/96.26 X |
| 4,336,809 | 6/1982 | Clark | 128/303.1 X |
| 4,423,726 | 1/1984 | Imagawa et al. | 219/121 LZ X |
| 4,454,882 | 6/1984 | Takano | 128/395 |
| 4,469,098 | 9/1984 | Davi | 219/121 LM X |
| 4,476,875 | 10/1984 | Nilsson et al. | 128/666 |

FOREIGN PATENT DOCUMENTS 2493533 5/1982 France ............................ 128/303.1

Primary Examiner—C. L. Albritton
Attorney, Agent, or Firm—Orrin M. Haugen; Thomas J. Nikolai; Frederick W. Niebuhr

[57] ABSTRACT

A control system for an optical fiber laser power delivery system wherein the system employs a tip assembly for the optical fibers which provide focusing and beam divergence, mechanical protection for the optical fibers, and in addition functions as the source of a condition responsive signal useful in monitoring and controlling the system operation. The tip assembly utilizes a synthetic sapphire lens or window having incident laser radiation and temperature dependent fluorescing property useful in generating a signal utilized in a feedback control system for the laser system. The improved tip assembly accordingly has application as an optical fiber shield as well as a signal source for the control and monitor portion of the laser system.

14 Claims, 8 Drawing Figures

FIBER TIP MONITORING AND PROTECTION ASSEMBLY

BACKGROUND OF THE INVENTION

The present invention relates to a control system for an optical fiber laser power delivery system wherein the system employs a tip assembly for the optical fibers which provides a number of advantages for the delivery system including control of beam focus and beam divergence, mechanical protection for the optical fiber and in addition, functions as the source of a condition responsive signal utilized in an associated laser monitoring and control mechanism. While providing a response for a variety of conditions, the tip assembly of the present invention responds to a temperature parameter which is dependent upon a number of conditions including optical fiber integrity, contamination at the discharge site, or the like.

The tip assembly of the present invention employs a synthetic sapphire shielding lens which, in addition to its desirable mechanical, optical and focusing properties, has a light and temperature sensitive fluorescing property useful in generating a signal utilized in a feedback control system for the laser system. With a laser functioning at a given or known power input level, the light and temperature sensitive fluorescing property of the sapphire lens or window creates a signal indicative of certain conditions existing at the tip of the optical fiber, including laser power being transmitted and tip temperature. The improved tip assembly accordingly has application not only as an optical fiber shield but as a signal source for one control and monitor portion of the laser system. The tip assembly of the present invention may be utilized in any of a variety of systems utilizing laser power, with the tip assembly being particularly well adapted for use in a laser enhanced transluminal angioplasty catheter where it functions to mechanically protect the optical fibers and also provide a feedback signal for use in monitoring the output of the laser energy at the tip of the fiber and also the temperature of the tip of the fiber.

The tip assembly and its associated control system provides a closed-loop arrangement for monitoring and controlling the output of the laser, with the closed-loop system having condition responsive signal generating means disposed at the desired delivery or treatment site within predetermined and/or preset limits. When utilized in angioplasty catheter applications, the distal portion of the system, including the improved tip assembly of the present invention, is preferably utilized as a component which may be readily coupled into and de-coupled from the other portions of the system.

The tip assembly used in the combination of the present invention employs a lens or window fabricated from synthetic sapphire or other suitable substance, with the lens being positioned concentrically with and adjacent to the distal tip end of an enclosed or sheathed optical fiber. The synthetic sapphire lens or window device emits energy in the form of fluorescent light in response to excitation with laser power, and also when heated to an elevated temperature. Since the intensity of the signal emitted by the sapphire lens in response to exposure to incident laser power is temperature dependent, the power level of the laser energy being transmitted through the fiber onto the tip and the temperature of the tip may be determined. As indicated above, the thermal condition of the sapphire lens in the tip provides an indication of the integrity of the overall delivery system as well as an indication of any anomaly which may exist in the tip area and/or the delivery system. The improved tip assembly of the present invention further provides a means to deliver or to transmit laser power to the required location, with the optical properties of the synthetic sapphire lens being capable of determining the focus or optical pattern of the fiber output, while simultaneously providing a source for a signal useful in monitoring the condition of the delivery system for the laser power, as well as the condition adjacent the exterior of the tip as represented by the thermal response or the temperature condition.

The monitor, control, and/or condition responsive feature of the present invention is enabled by utilizing a lens responsive to laser power and temperature for determining certain of the conditions existing within as well as along the optical fiber delivery mechanism as well as to conditions existing at or immediately adjacent the point at which radiation in the form of a laser beam is being discharged from the tip. In the assembly illustrated in the drawings, the inner surface or end of the lens is fixedly disposed adjacent the optical fiber tip and the outer surface or end is immersed in or otherwise subjected to the environment into which the laser beam power output is delivered. Because of its arrangement in the system, the condition responsive lens is ideally situated and suited to function as a sensor responsive to certain conditions, including laser power, or deliver system integrity and/or conditions existing in the zone receiving the laser beam power. Each of these conditions may be determined by an evaluation of the temperature of the artificial sapphire lens body through its fluorescent behavior. In addition to fluorescence of the lens as a function of laser light intensity and lens temperature, other fluorescent signals may be generated during operation of the laser, including, for example, signals generated due to fluorescence of certain materials used in fabricating an angioplasty catheter, as well as other signals obtained from materials or matter receiving laser power, including the optical cable. The most significant flourescent signal created during operation of the system is that created by the fluorescent behavior of the lens body. The signal emitted from the lens will be fed back through a portion of the laser beam delivery system, filtered, and its amplitude determined electro-optically. In other words, the amplitude of the flourescent signal obtained from the lens will be determined electro-optically, and the value obtained is compared to the value which is expected from the input to the laser. The "window" is a range of values within performance tolerances. Deviation of this signal from a window representative of an optimum signal value or range of signal values will be indicative of one or more malfunctions including, for example, unacceptable performance of the delivery system, or the existence of contamination or accumulation of debris in the zone receiving the beam energy. In operation, therefore, a sensed deviation from a certain value or window of values will normally be utilized to trigger the shut-off or interruption of flow of energy from the laser unit. A value which falls below a certain range of output values may indicate a malfunction in either the laser unit per se or in the intermediate delivery system, and may be indicative of a broken optical fiber, or fiber tip damage. Such an indication will be utilized to trigger system shut-off or the interruption of flow of energy from the laser unit.

The lens forming a portion of the tip assembly performs a number of functions in addition to the generation of a flourescent signal. For example, the lens is utilized as a focusing element for the beam of laser radiation exiting the fiber tip. This radiation is focused along a cone which converges to a focal point. In this manner, the radiation from the laser is normally dispersed in a pattern or profile representative of an expanding or diverging cone beyond the focal point. In addition, the tip assembly acts as a means to isolate or protect the fiber tip from debris build-up or corrosion when the system is being utilized in an unclean or harsh environment. When fabricated of metal or radiopaque material, it may be utilized as a tip identifier in angioplasty procedures.

In one system employing features of the present invention, a lens system is utilized which includes a synthetic sapphire lens body which functions as a sensor emitting fluorescent radiation within a certain predetermined wavelength when excited with coherent radiation from a laser source. The amplitude of the emitted signal is sensitive to temperature, so that system performance and delivery system integrity may be measured against predetermined values for various known power input levels. The emitted fluorescent radiation from this sensor has a wavelength which is detectably different from that of the incident laser radiation. The sensor, when at an appropriate operating temperature, such as within a predetermined window of operating temperatures, and while transmitting or passing a predetermined amount of laser power therethrough, emits a fluorescent radiation signal having a magnitude, intensity or level indicative of its temperature and the laser power. When the signal is within predetermined desired upper and lower tolerance limits, as determined by a comparision with a known and acceptable signal obtained from the sensor when operating at its anticipated temperature and laser power levels, the entire system is permitted to continue to function. Since the fluorescent signal, as detected, may constitute the sum of a number of such signals from components other than the tip, such as from the catheter material or the fiber optical material, the ultimate signal obtained will be the resultant or composite of a number of components or inputs. Accordingly, when the temperature level of the synthetic sapphie tip sensor is either above or below the anticipated or desired level, a fluorescent signal (having a detectably different magnitude or level) will be created which falls outside of the window. In other words, whenever a uniform and predetermined amount of laser power is being delivered to the sapphire tip, the fluorescent response is a function of the incident laser power and the temperature of the sensor. When systems employing sensors of the type described, have been calibrated, readings indicative of departures from predetermined output power levels and predetermined tip temperature levels may be detected. While the readings obtained may not readily translate into indications of absolute temperature or the like, it has been found that these readings do indicate proper operating conditions, both on the fiber side of the tip and on the exterior. Once a system has been properly calibrated, the flourescent response of the synthetic sapphire tip may be utilized as a measure of proper overall system operation.

Synthetic sapphire is an appropriate choice of lens material. The wavelength of an output beam from an Argon ion laser will normally fall within the absorption band of a chromium-doped synthetic sapphire body. It will be appreciated that synthetic sapphires containing dopants other than chromium, as well as certain other synthetic crystalline materials other than sapphire may respond in a manner such that they may be useful in systems of the present invention. However, it has been found that synthetic sapphire, slightly doped with chromium ions within a relatively low doping level, such as in the range of approximately 20 ppm provides a fluorescing signal of a useful level when exposed to high intensity laser light, such as that received from an Argon ion laser. This signal is obtained without significant loss or degradation of the laser energy passing through the synthetic sapphire. Impurities, other than the intentionally added chromium ions, are selected or controlled at minimum levels so that exceptionally low absorption and/or minimal interferring fluorescent responses are obtained upon exposure to laser radiation within the wavelength of the laser used.

The system of the present invention is designed for use with a laser beam of moderate or long duration. In this connection, however, if output pulses of known duration are employed, an indication of tip temperature may be obtained by obtaining a measurement of the decay time of the fluorescent output.

The power level of the output or response of the synthetic sapphire is inversely proportional to its temperature. Such response is typical for chromium-doped synthetic sapphire. Additionally, as the doping level of chromium ions increases, at least up to a certain range or level, the fluorescing activity also increases. It has been found that relatively low doping levels, such as in the range of 20 ppm of chromium ions, provide synthetic sapphires with a lens body having the desired fluorescent response, with this response being obtained with a minimum of losses of laser output power being transmitted through the sapphire.

While the terms "fluoresce" or "fluorescent" are used herein, it is to be noted that these terms are being used in a comprehensive sense so as to include generally the emission of light upon stimulation from another light source, and wherein the wavelength of the emitted light of the sensor element may or may not fall within the visible range for the human eye. The emitted light is normally at a wavelength longer than that of the stimulating light energy.

While the tip assembly and associated laser catheter monitor-control apparatus of the present invention has general utility for various systems employing laser beam energy, the tip assembly and its associated monitor-control is particularly adapted for use in combination with laser devices for a variety of medical end-uses, with one such end-use being in combination with laser enhanced transluminal angioplasty catheter devices. As is known, laser devices have been found useful in treatment of a number of conditions, including treatment of some forms of arteriosclerosis. Laser enhanced angioplasty catheter devices are useful for treatment of certain types of obstructions or occlusions formed, created or otherwise present in blood vessels such as those created and encountered due to plaque build-up or the like. Exposure to laser beam energy is undertaken in order to obtain either a partial removal, reduction and/or the elimination of the obstruction by means of such exposure. In such systems an optical fiber member is typically utilized for receiving, transmitting or otherwise conducting a beam of laser energy from a generator onto a remote output lens for precise delivery or discharge of the laser energy from the lens and onto or against the plaque or other matter obstructing or occluding a blood vessel. While the extent of exposure to laser beam energy may be controlled by selecting and regulating the extent of on-time of the laser, the power level involved, and/or the energy distribution at the distal tip of the fiber, it is, nevertheless, desirable to monitor the overall operation of the laser system so that any unusual variation in output power, ambient or environmental conditions may be detected, including either excessively high or unusually low power levels being delivered to the tip. The system of the present invention provides a means for determining the operating condition of the laser beam generator, its transmission system, and its operating ambience, by precisely determining the laser power output and the magnitude of the temperature change existing at the output end, thereby providing a means for alerting the user to the existence of certain operational anomalies. By way of example, operational anomalies may occur if the generator is driven with an unusually high or unusually low amount of input power, with another operational anomaly occurring if one or more beam transmitting fibers become cracked, fractured or displaced from the surface of the lens tip.

When utilized as a laser catheter monitor-control system in combination with laser enhanced transluminal angioplasty catheter devices, the apparatus of the present invention is useful in combination with those certain laser catheter control and connecting apparatus disclosed and claimed in co-pending applications Ser. No. 679,633, filed Dec. 10, 1984, and Ser. No. 679,920, filed Dec. 10, 1984, each being assigned to the same assignee as the present invention and reference may be made to the disclosure contained therein.

The embodiment of the tip assembly and monitor-control system of the present invention as illustrated herein is shown as functioning within a laser enhanced transluminal angioplasty system, it being understood that such a system is illustrated for purposes of explaining the fundamental operational features of the system and not by way of limitation.

SUMMARY OF THE INVENTION

An improved fiber tip assembly and associated monitor-control system is provided, with the arrangement being particularly adapted for use in a laser enhanced transluminal angioplasty system or any other laser power delivery system. The overall system comprises a laser beam generator, a fiber optic laser beam transmission system, and a distal tip assembly having a beam divergence and/or focusing optical element, with the optical element being responsive to laser power transmission levels and to temperature so as to function as the source of a signal indicative of those conditions. The optical element is a form of synthetic sapphire doped with chromium ions. These systems have been found particularly adapted for use with the outputs of lasers such as Argon ion or Nd-YAG lasers. Other lasers may, of course, be adapted for use in combination with the arrangement of the present invention as well. Other doping material can be used to adapt to different laser wavelengths. The light transmission systems utilized with these lasers, particularly in medical applications typically include light transmitting fibers normally referred to as optical fibers, which terminate at the surface of the chromium ion-doped synthetic sapphire lens or tip. Normally, the optical fibers are disposed in substantial abutment with the surface of the lens. During normal operation, the lens emits radiation of a wavelength and at a level indicative of, or responsive to, the level of laser power transmitted through the optical element, and also responsive to or indicative of their thermal condition or temperature level. The emitted radiation has a level or amplitude which may be detected, quantified and compared to a known level indicative of normal operation. When operational anomalies exist such as stressed fiber, contaminated distal tip, contaminated or damaged fiber connector and broken fiber somewhere in the system, the detected level of emitted radiation will be different from that expected or anticipated. In other words, the chromium ion-doped synthetic sapphire tip functions not only as a protective shield, but more importantly as a source which emits fluorescent radiation when excited with laser beam or other radiation within a certain bandwidth. The radiation so emitted has a characteristic wavelength which is also detectably different from the incident laser power and is emitted at a level which is inversely proportional to the actual temperature of the lens.

Synthetic sapphire is the preferred material for the optical lens. Such materials are, of course, commercially available, being fabricated as a boule from aluminum oxide by a single crystal growing technique, such as, for example, by the Czochralski Technique. The advantages of use of synthetic doped sapphire in the present arrangement stems from their optical properties, as well as their mechanical properties. Additional advantages include their high temperature stability and durability as well as their biochemical neutrality.

The fiber tip monitoring and protection assembly of the present invention provides a means for continuous monitoring of the integrity and the operational status of a fiber optic delivery system. The arrangement provides for continuous evaluation of the level of laser power reaching the tip, and further provides for constant indication of the temperature condition at the tip end. The arrangement of the present invention provides a means to interrupt, terminate, or otherwise discontinue delivery of laser power to the tip when it is determined that the laser power output at the distal tip is not within predetermined limits, or alternatively that the temperature at the tip end is not within predetermined limits.

Therefore, it is a primary object of the present invention to provide an improved tip assembly and laser monitor-control system which utilizes a shielding lens which emits fluorescent radiation when excited with incident laser radiation transmitted through the lens, and wherein the radiation so emitted has a wavelength which is detectably different from the incident laser radiation, and wherein the output level of the emitted radiation is dependent upon the power level of the incident radiation and the temperature of the lens.

It is a further object of the present invention to provide an improved tip assembly for an optical fiber laser beam delivery system employing a chromium ion-doped synthetic sapphire lens element, and wherein means are provided to control the operation of the laser system through detection of fluorescent radiation emitted from the chromium ion-doped synthetic sapphire lens, with the level of the emitted radiation being dependent upon the incident power and lens body temperature, thereby providing an indication of certain operational parameters within the system and within the system ambience.

Other and further objects of the present invention will become apparent to those skilled in the art upon a study of the following specification, appended claims, and accopanying drawings.

IN THE DRAWINGS

DESCRIPTION OF THE PREFERRED EMBODIMENT

Figure 1:
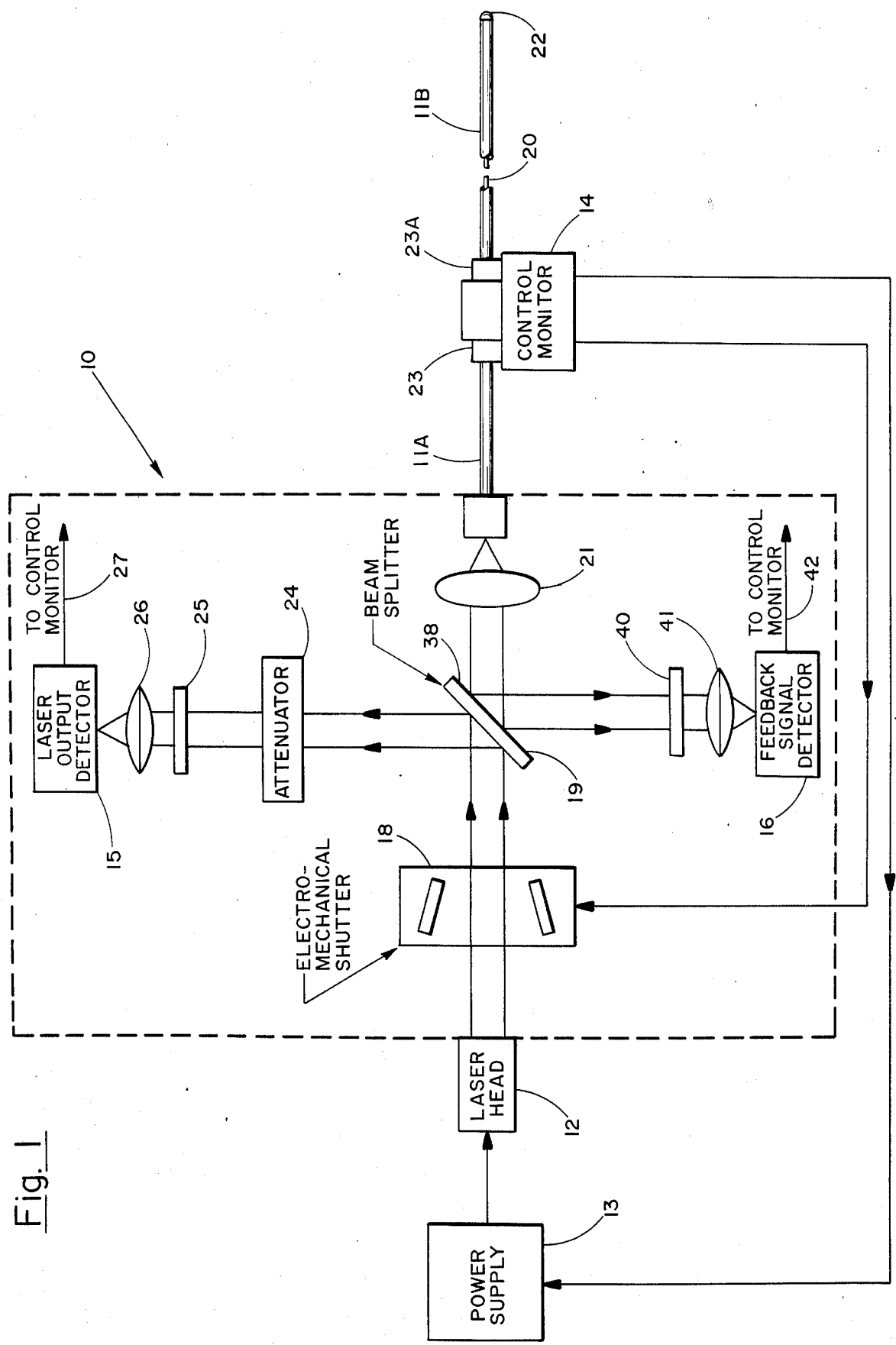
FIG. 1 is a schematic diagram, partially in block form of the tip assembly and associated monitor-control system of the present invention, showing the arrangement embodied in a laser-enhanced transluminal angioplasty catheter system.

With particular attention being directed to FIG. 1, the schematic block diagram portion thereof and the remaining features depict a laser-enhanced transluminal angioplasty catheter system embodying the tip assembly of the present invention. This system, generally designated 10, comprises a transluminal angioplasty catheter arrangement which is equipped or provided with a means to deliver laser power. Optical fibers are utilized for transmission of the laser energy, with a first optical fiber segment 11A being utilized to conduct laser power into control monitor 14, and with a second optical fiber segment 11B being utilized to transmit laser power from control monitor 14 to the output tip. The laser system comprises a laser head 12 powered by power supply 13, with power supply 13 being controlled by control monitor 14 which is coupled to receive inputs from laser output detector 15 and feedback signal detector 16. The power output beam from laser head 12 is passed outwardly from the head and onto electromechanical shutter 18, and thence onto beam splitter 19. Electromechanical shutter 18 may be actuated from the control unit for safety purposes as discussed hereinafter. Beam splitter 19 passes most of the incoming radiation from laser head 12, with this transmitted radiation then passing through focusing lens 21 and into the proximal end of the optical fibers 20 disposed within segments 11A and 11B, and ultimately exiting from tip 22. The items contained within the dotted line of FIG. 1 are those items which are normally contained within a fiber optic coupling system enclosure either at or mounted on the head of the laser. Normally, tip 22 will have an outer diameter less than the outer diameter of the tube portion of segment 11B, but due to limitations of draftmanship, the outer diameters are shown as being substantially equal in FIG. 1.

Control monitor 14 is interposed between focusing lens 21 and tip 22, and optical fiber segments 11A and 11B are coupled to control monitor 14. Segments 11A and 11B are coupled to control monitor 14 by means of conventional optical fiber-to-fiber connectors. In other words, optical fiber segment 11A transmits laser energy from focusing lens 21 into control monitor 14, with a fiber-to-fiber connector designated at 23/23A being utilized to couple the laser energy into the catheter portion of the system, such as into optical fiber segment 11B.

Beam splitter 19 may be in the form of a dichroic beam splitter, and is normally mounted with its surface at an angle of approximately 45° with respect to the axis of the incident beam, thus continuously sampling the laser source, while permitting the majority of the laser power to be transmitted therethrough. In addition to reflecting a portion of the incident radiation, beam splitter 19 simultaneously functions to reflect the feedback signal propagating from fluorescing sapphire 22 at a distinguishable and characteristic wavelength In this fashion, therefore, beam splitter 19 directs the energy sampled from the laser source onto laser output detector 15, and furthermore directs the fluorescent feedback signal to feedback signal detector 16 from the fluorescing sapphire 22. In this arrangement, the fluorescent signal energy passes through the laser catheter fiber 11B, into the connecting fiber 11A and through the focusing lens 21-21 onto the beam splitter 19. The optical fibers 20 terminate at tip assembly generally designated 22, after passing through optical fiber-to-optical fiber connectors 23 and 23A, normally a butt-joint, forming an optical connection between the connecting fiber 11A and the catheter fiber 11B. Trailing segment 11B which is disposed between control monitor 14 and tip assembly 22 is normally in the form of a disposable catheter and typically in the form of a balloon catheter of the type shown in applications Ser. Nos. 679,633 and 679,920, supra. When utilized as a laser enhanced angioplasty device, the trailing segment 11B may be detachably coupled to the system through the optical fiber connector pair 23 and 23A. Accordingly, optical fiber segment 11A represents a permanent interconnecting fiber between control monitor 14 and the optical coupler 10 on or at the head of the laser housing the components contained within the dotted line enclosure.

Beam splitter 19 directs or deflects a portion of the incoming laser beam energy onto threshold detector 15, with such deflected energy passing through attenuator 24, filter 25 and lens 26 before reaching laser output detector 15. Laser output detector 15 is a typical electro-optical detector having a comparator means to determine whether or not the strength of the deflected portion of the beam is within normal operational parameters. In this fashion, therefore, laser output detector 15 is adapted to generate an electrical signal which is delivered to the control monitor through the conductor system as at 27 in order to permit continued operation of the system, or alternatively to interrupt such operation. Detectors of the type employed in the system, such as laser output detector 15 are readily commercially available. In operation, therefore, when the strength of the deflected signal from the beam splitter 19 is not within predetermined values, the system electronics in the control monitor will function to close shutter 18, which effectively interrupts and/or terminates system output.

Figure 2:
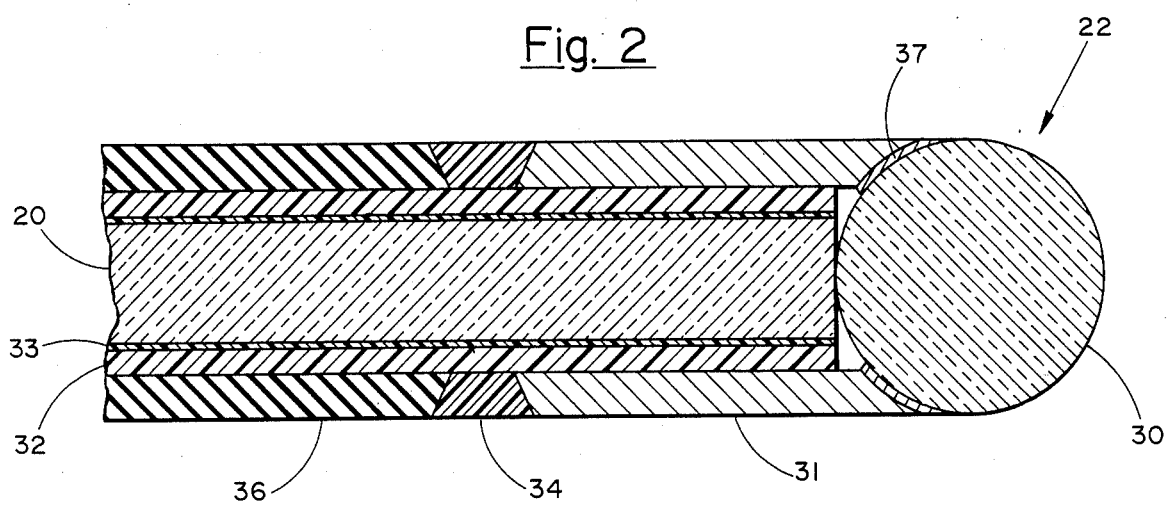
FIG. 2 is a detail sectional view, taken through the diameter, of the tip assembly and illustrating the configuration of the optical element employed at the output end of the system, and illustrating the optical element in a solid sphere configuration.

With attention being directed to FIG. 2 of the drawings, and with continued attention being directed to FIG. 1, tip assembly 22 comprises a spherical lens 30 retained within a radiopaque metallic sleeve element 31, with sleeve element 31 surrounding optical fiber 20 contained therewithin. This metallic sleeve also serves as an identifier of the tip of the fiber under fluoroscopy. Lens 30 functions as a window at the distal tip of the optical fiber, and further functions as an emitting source of a light signal of a different wavelength when excited by the laser power or radiation. Metal sleeve 31 is preferably a fine metallic tube, but may alternatively be fabricated from ceramic or glass, and is arranged to enclose the far-tip of the polished optical fiber on one end, and an optical element, capable of fluorescing, on the other end. Fiber 20 is coated with a high strength buffer sleeve and a protective biologically compatible buffer sleeve 36. The high strength buffer sleeve may be in the form of a polyimide sheath 32, it being understood that other synthetic resins with good high temperature properties may be used as well. A conventional fiber-cladding film 33 is shown surrounding the core of fiber 20. An adhesive bond, preferably an epoxy adhesive, is applied so as to wick-up under tube 31, thereby providing a sound and firm bond between tube 31 and coating 32. In this fashion, a suitable bond is established between metal sleeve 31 and the conventional biocompatible coating 36. A commercially available biocompatible coating sold under the designation "Tefzel", among others, may be employed as a material for coating 36. A ceramic-to-metal seal zone is illustrated at 37, which is typically a high quality ceramic-to-metal seal providing a hermetic bond or seal within the confines of the tip assembly. While certain metals may be employed to form the ceramic-to-metal bond, eutectic metal seals are normally employed and are generally preferred. While those bonding materials typically designated "ceramic-to-metal" seals are preferred, it is understood that certain glass bonding materials may be employed as an alternative to the ceramic-to-metal bonds.

With attention again being directed to FIG. 1 of the drawings, synthetic sapphire spherical lens 30 responds to incident laser power by emission of a fluorescent signal. The lens is responsive to laser radiation within the wavelength of Argon ion lasers and to the temperature conditions of the lens as well. The emitted signal from lens 30 is transmitted back to beam splitter 19 along the optical fiber 20, with the distal face 38 of beam splitter 19 serving to deflect the emitted signal onto filter 40, lens 41, and ultimately to feedback signal detector 16. Filter 40 is a narrow band interference filter, which is preferably placed in front of lens 41 and feedback signal detector in order to pass only the feedback signal wavelength. Feedback signal detector 16 is a conventional electro-optical device and generates an electrical signal which passes along line 42 to control monitor 14. The control monitor 14 gathers, monitors, compares, processes and may display all data received from the detectors as well as the electrical and mechanical drives. Control monitor 14 is provided with a means to actuate electromechanical shutter 18 so as to interrupt flow of laser power through the system in the event of the detection of a malfunction condition at any time during normal operation. The level of signal generated by feedback signal detector 16 is, of course, representative of the output power of the laser received at spherical lens 30 and its fluctuation indicates the relative temperature change experienced by lens 30. The level or amplitude of the signal will provide a further indication of whether or not the system is operating within its desired output power and temperature limits.

When utilized in combination with a transluminal angioplasty catheter, metal tube or sleeve 31 provides the presence of a radiopaque member or element which assists in normal laser angioplasty procedures. The availability of such a component adjacent the tip of the device is, of course, helpful and useful in typical laser angioplasty procedures. Also, in order to achieve a symmetrical output radiation pattern for delivery of the laser power, the optical fiber, the spherical tip 30, and sleeve 31 should be arranged coaxially.

The chromium-doped artificial sapphire sphere 30 functions as a positive lens to focus the laser beam energy exiting the fiber tip at a short distance from the lens surface. Beyond the focal point, the energy is dispersed along an expanding cone pattern. The polishing finish for the surface of the sphere 30 directed toward the laser light transmission are necessarily extremely smooth with the limiting size for surface defects being no greater than dig-scratch sizes of 10-5 so as to minimize scattering losses. The dig-scratch index is obtained pursuant to procedures set forth in Military Specification designated "M1L-0-13830A", dated Sept. 11, 1963.

The tip assembly, as has been indicated, provides a hermetic seal for the distal end of the fiber 20. Optical fiber 20 is provided with a polished distal end, and is inserted within tube or sleeve 31 to a point in substantial abutting relationship with spherical lens 30. Tube 31 along with epoxy bonding fillet 34 accordingly maintain these components of the system with a high degree of integrity. Furthermore, epoxy fillet 34 is preferably provided to a level sufficient to fill the space or gap existing between the sleeve 31 and the outer buffer sleeve of the fiber, such as Tefzel coating 36 and also with modest internal wicking. This provides the outer diameter of the assembly with a smooth surface, with a minimal transition cone. Also, it will be noted that in the illustration of FIG. 1, tip assembly 22 is illustrated having a tip portion which has a diameter greater than that of the optical fiber or fibers 20. Because of limitations of draftsmanship, this element is shown, in FIG. 1, as having a slightly larger diameter.

Accordingly, tip assembly 22 provides effective isolation of the fiber tip from the surrounding environment. Such isolation eliminates any problem that may arise due to debris build-up or corrosion of the tip of the optical fiber 20 whenever the system may be used in an unclean, wet, or with chemicals creating a harsh environment.

As may be appreciated, the tip assembly is fabricated from components which are durable, and hence resistant to harsh chemicals, moisture, either high or low temperatures, scratches, mechanical stresses, as well as being predictably responsive or reactive to electromagnetic fields. Such an assembly increases the durability of the entire system, and increases its reliability above that which may be expected from the optical fibers standing alone. Furthermore, when prepared from durable and resistant components, the assembly may be sterilized in a variety of fashions, including those typically employed in a hospital environment without adversely affecting the integrity or performance of the system when used in medical applications.

The utilization of a metal sleeve provides ease of identification and location of the optical fiber tip with respect to the catheter system fluoroscopically when used in any remote visibly opaque environment, such as within the human body. In such applications, the compactness of the tip assembly is such that its versatility of use is essentially the same as that of the optical fiber alone, and extended beyond such versatility when considering the use of durable and resistant materials of construction for the components.

The tip element 30, such as the sphere illustrated in FIG. 2, provides a means of focusing the laser power along a converging cone to a defined focal point, and beyond the focal point, the laser power is spread in a wider angle than the fiber exiting beam alone. Such focusing power is not available in an optical fiber alone. Furthermore, the optical performance of the sphere aids in collecting optical radiation surrounding the optical fiber tip whenever the system is used for monitoring the conditions existing at a remote site. In addition, the utilization of the optical element adjacent the fiber tip permits usage with a fiber imaging system.

In addition to the uses discussed hereinabove, the optical element, such as the artificial sapphire spherical lens 30 provides a feedback signal which is related to the output power of the laser being delivered at the fiber tip and to the temperature of the sapphire lens element and its ambience or surroundings. The level of the feedback signal is indicative of the condition existing at the tip, and particularly the temperature of the spherical lens and the level of laser power being transmitted through the system to the sphere. A condition which may be discovered through the utilization of the feedback signal is that of integrity of the optical fiber delivery system, or stated another way, the presence or absence of fiber breakage or tip damage or contamination. Based upon the level of the signal obtained through the feedback system, the overall arrangement may be used as a sensor for detecting temperature changes, ambient pressure or other environmental parameters. With the ultimate temperature limits being known, conventional techniques may be utilized to calibrate the system so as to correlate or compare the response in accordance with the indicated conditions.

Figure 3:
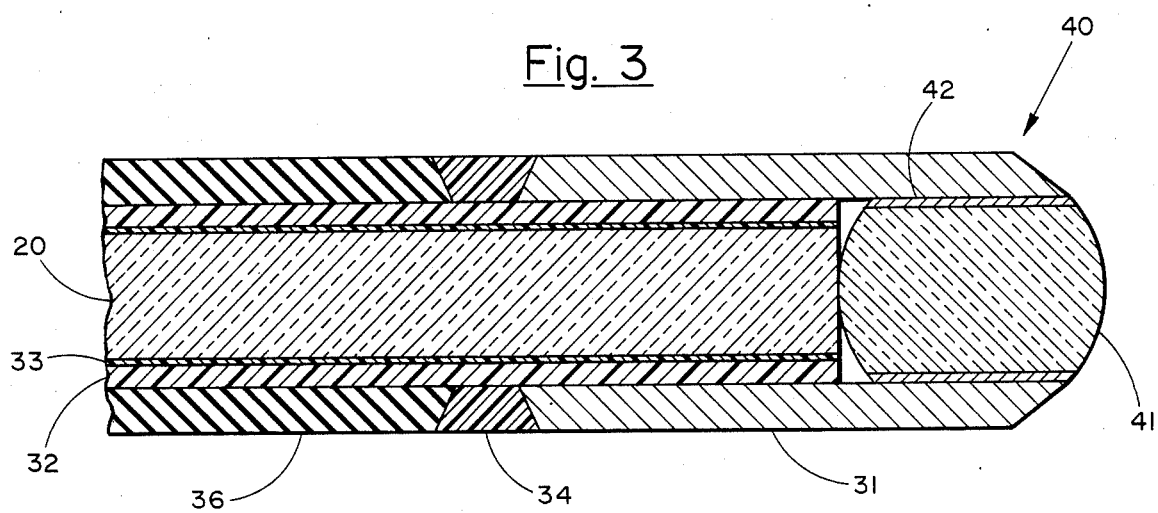
FIG. 3 is a view similar to FIG. 2, and illustrating the optical element in the form of a double-dome as fabricated from a ball or rod stock.

Attention is now directed to FIG. 3 of the drawings wherein a modified form of tip assembly is shown. Specifically, tip assembly generally designated 40 comprises an optical element or distal tip element 41 in the form of a double-dome lens. Element 41 is secured to sleeve 31 by annular ceramic-to-metal seal 42. The material of construction for element 41 is, of course, the same as that of element 30, as are the remaining components of the tip assembly 40 as related to the structure illustrated in FIG. 2. As has been indicated, the double-dome lens or optical element 41 may be fabricated from either a ball element, or alternatively, from a rod element.

Figure 4:
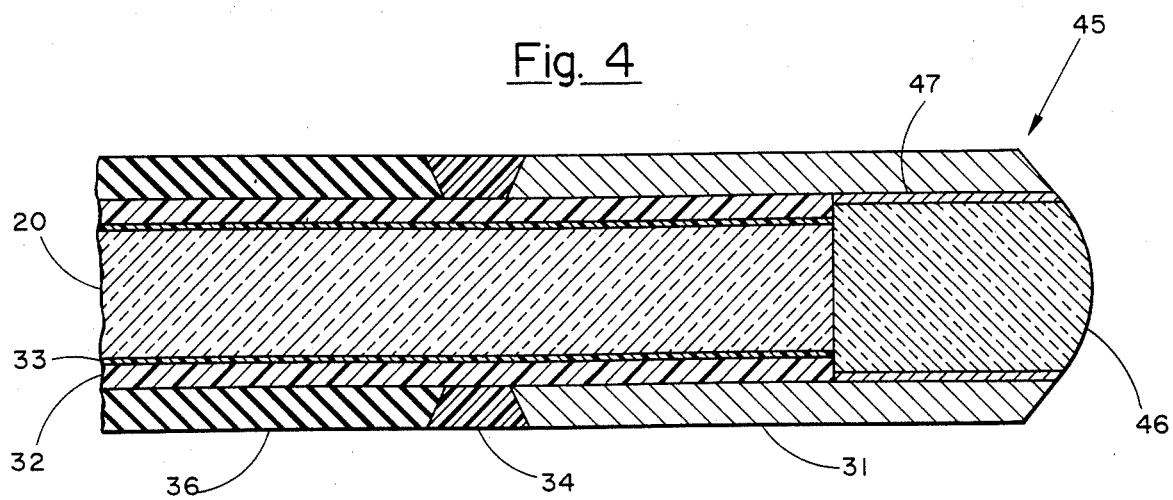
FIG. 4 is a view similar to FIG. 2 illustrating the optical element in the form of a single-dome.

In FIG. 4 of the drawings, a further modified form of tip assembly 45 is illustrated. A single dome optical element or lens 46 is disposed at the distal tip end thereof. Lens 46 is maintained within metal sleeve 31 by ceramic-to-metal seal 47, with seal 47 being in the form of an eutectic metal seal. Such seals may be obtained commercially. The remaining elements and components of tip assembly 45 are the same as those illustrated and explained in detail in FIG. 2.

Figure 5:
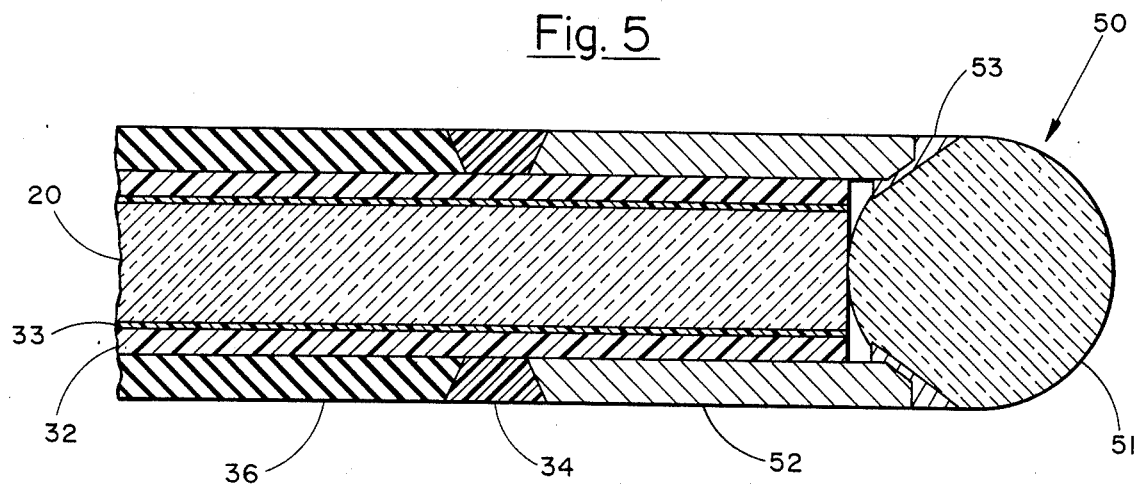
FIG. 5 is a view similar to FIG. 2 and illustrating the optical element in the form of a conically recessed sphere.

Attention is now directed to FIG. 5 of the drawings wherein tip assembly 50 is illustrated, and having a modified form of optical element or lens 51 arranged at the distal tip end thereof. Optical element or lens 51 is secured to metal sleeve member 52 by means of ceramic-to-metal seal 53. Seal 53 is fabricated as an eutectic metal seal, with such seals being obtained commercially. The configuration of the optical element 51 in FIG. 5 is that of a sphere with a conical recess formed therein.

Figure 6:
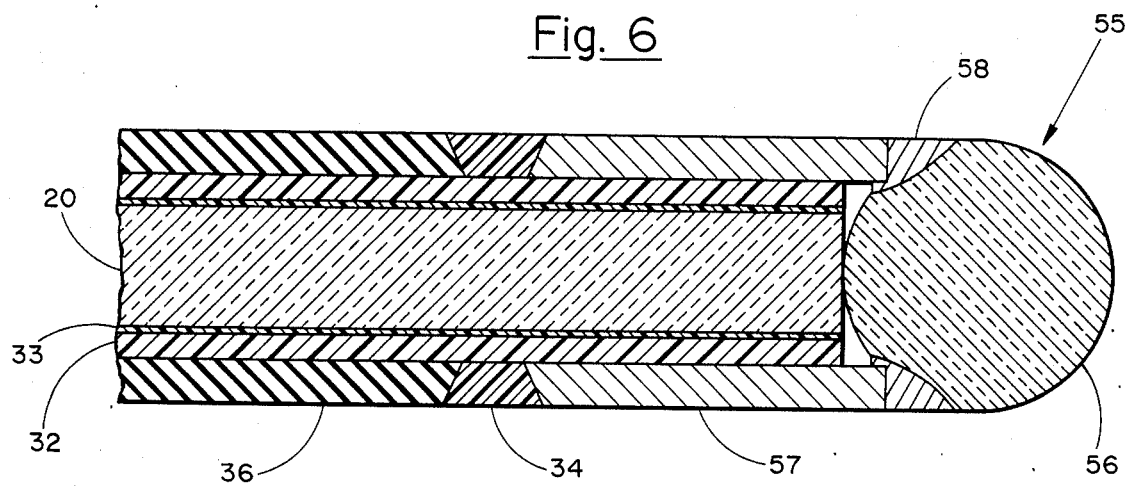
FIG. 6 is a view similar to FIG. 2 and illustrating the optical element in the form of a sphere having a concave radial recess formed therein.

Attention is now directed to FIG. 6 of the drawings wherein a still further modified form of tip assembly 55 is illustrated. Tip assembly 55 utilizes an optical element or lens 56 together with a metallic sleeve 57. Optical element or lens 56 is retained in place with sleeve 57 by means of ceramic-to-metal seal 58, with seal 58 being fabricated in the same fashion as that corresponding seal illustrated in FIGS. 2-5 inclusive. Optical element or lens 56 is, in this instance, fabricated as a sphere having a radial recess formed therein. In certain instances, a synthetic sapphire element having a cylindrical configuration may be employed.

Figure 7:
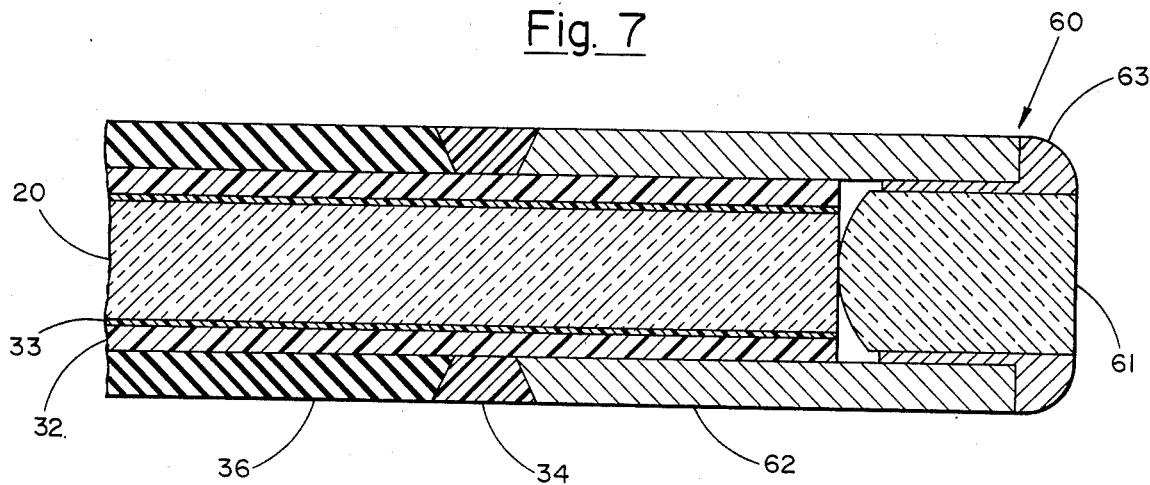
FIG. 7 is a view similar to FIG. 2 and illustrating the optical element in the form of a reversed single dome.

In FIG. 7 of the drawings, a further modified form of tip assembly is illustrated, with the optical element being in the form of a reversed single dome. Tip assembly generally designated 60 utilizes an optical element or lens 61 together with a metallic sleeve 62. Optical element 61 is retained in place within sleeve 62 by means of ceramic-to-metal seal 63, with seal 63 being fabricated in the same fashion as that corresponding seal illustrated in FIGS. 2-6 inclusive. Optical element or lens 61 is, in this instance, fabricated as a cylinder having a proximal end formed as a segment of a sphere. The material for optical element or lens 61 is preferably synthetic sapphire as discussed hereinabove.

Figure 8:
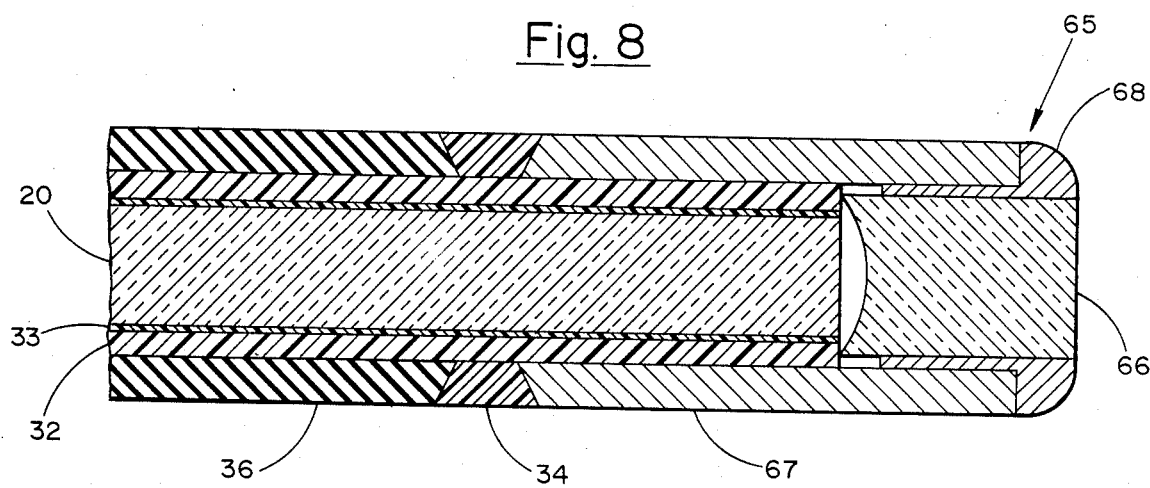
FIG. 8 is a view similar to FIG. 2 and illustrating the optical element in the form of a negative lens.

With attention now being directed to FIG. 8 of the drawings, a still further modified form of tip assembly is illustrated. Tip assembly generally designated 65 utilizes an optical element 66 together with metallic sleeve 67. Optical element 66 is retained in place within sleeve 67 by means of ceramic-to-metal seal 68, with seal 68 being fabricated in the same fashion as that corresponding seal illustrated in FIGS. 2-7 inclusive. Optical element or lens 66 is, in this instance, fabricated as a negative lens formed as a cylinder having a spherical recess formed in the proximal end thereof. The material of construction for lens 66 is preferably synthetic sapphire as hereinabove. This configuration will enhance the diverging beam and minimize the stress induced by the high laser energy on the optical element.

The operation of the system of the present invention is based upon the utilization of re-radiated or fluorescent light energy being generated at the far distal tip of the light transmitting optical fiber. The optical element which creates the re-radiated energy is essentially an element which fluoresces when excited by the source light and in the system described above, the fluorescent output is inversely proportional to the temperature of the body comprising the optical element and directly proportional to the incident laser radiation. This re-radiated or fluorescent energy is fed back along the fiber optic delivery system to a control. The re-radiated signal is monitored constantly while the source energy is being delivered to the target. The outputs of the threshold detector 15 and emitted signal detector 16 are applied to control monitor 14 through lines 27 and 42 respectively, so that these outputs can be used to obtain a desired error signal or threshold which may reduce the creation of problems due to laser output power fluctuations.

It will be appreciated that various modifications of the invention may be devised by those skilled in the art.

What is claimed is;

1. In a control system for use with a laser generated radiation system utilizing, in combination, a laser generator, a lens means, and an optical fiber for transmission of radiation in the form of laser energy from the generator to the lens, the lens means comprising a laser energy transmitting lens body with a pair of opposed surfaces, one of said surfaces being arranged for reception of an incoming beam of radiation from the distal tip end of an adjacent optical fiber and thence through said lens body; said control system comprising:
   (a) a laser generator for creating and discharging an output of laser energy as a beam of such energy and being within a certain first predetermined output power level and having a certain first predetermined wavelength;
   (b) a lens body transmissive to incident laser beam radiation within said first predetermined output power level and having a surface arranged for reception of an incoming beam of radiation at one end thereof and having an opposed surface arranged discharge of said beam therefrom;
   (c) an optical transmitting fiber arranged to receive radiation at the proximal end thereof from said laser generator and to transmit such radiation along the length thereof, said optical fiber having a distal tip end disposed adjacent a surface of said lens body;
   (d) said lens means emitting fluorescent radiation within a certain second predetermined wavelength upon excitation through exposure to said laser beam, said second predetermined wavelength being significantly different from said first predetermined wavelength; and
   (e) sensing means for detecting the radiation emitted from said lens body.

2. The control system as defined in claim 1 being particularly characterized in that said lens body consists essentially of synthetic sapphire.

3. The control system as defined in claim 2 being particularly characterized in that said synthetic sapphire is doped with chromium ions.

4. The control system as defined in claim 3 wherein said chromium ions are present in sapphire in the range of about 20 ppm.

5. The control system as defined in claim 1 being particularly characterized in that a radiopaque lens body retention sleeve surrounds said lens and is securely bonded to the periphery of said lens body and forms a hermetic seal therebetween and within the zone surrounding said radiation receiving surface.

6. The control system as defined in claim 1 wherein a portion of said optical transmitting fiber is arranged to receive radiation at the distal tip end thereof emitted by said lens means for transmission to said sensing means.

7. The control system as defined in claim 6 wherein said sensing means includes means provided along said optical transmitting fiber to interrupt the transmission of laser beam energy therealong.

8. In a control system for use with a laser generated radiation system utilizing, in combination, a laser generator, a lens assembly including a lens means, and an optical fiber for transmission of radiation from the generator to the lens means, the lens means comprising a lens body with a pair of opposed surfaces, one of said surfaces being arranged for the reception of an incoming beam of laser radiation from the tip end of an adjacent optical fiber and thence through said lens body; said control system comprising:
   (a) a laser generator for creating a beam of laser radiation within a certain first predetermined output power level and at a certain first predetermined wavelength;
   (b) a lens body within said lens assembly and consisting essentially of synthetic sapphire and transmissive to incident radiation within said first predetermined output power level and being arranged to receive laser beam radiation at one end thereof and to discharge said laser beam energy at the opposed end thereof;
   (c) an optical transmitting fiber arranged to receive laser generated radiation at the proximal end thereof and to transmit such radiation along the length thereof, said optical fiber having a distal tip end disposed adjacent the radiation receiving surface of said lens body;
   (d) a lens body retention sleeve within said lens assembly for receiving and retaining said optically transmitting fiber adjacent the distal tip end thereof and for maintaining said fiber distal tip end in a predetermined position relative to the radiation receiving surface of said lens body;
   (e) said lens body being adapted to emit fluorescent radiation within a certain predetermined wavelength upon exposure to radiation from said laser generator having an output power level within said first predetermined power level and with the strength of said emitted radiation being indicative of the intensity condition of incident laser beam energy and of the temperature of said lens body, and with said emitted radiation having a wavelength which is significantly different from said first predetermined wavelength; and
   (f) sensing means operatively associated with said optical transmitting fiber for detecting the radiation emitted from said lens body.

9. The control system as defined in claim 8 wherein chromium ions are present as a dopant in an amount ranging up to about 20 ppm.

10. The control system as defined in claim 8 wherein said lens body retention sleeve is in the configuration of an annular sleeve surrounding said lens body.

11. The control system as defined in claim 8 wherein said sensing means includes means provided along said optical transmitting fiber to interrupt the transmission of laser beam energy therealong.

12. In a control system for use with a laser generator, a radiant energy discharge assembly remote from said laser generator, and an optical fiber disposed mutually adjacent said laser generator and said energy discharge assembly for transmission of radiation from the laser generator to the radiant energy discharge assembly, the radiant energy discharge assembly comprising a radiant energy transmissive window with a pair of opposed surfaces, one of said window surfaces being arranged for the reception of an incoming beam of laser radiation from the tip end of said adjacent optical fiber and thence through said radiant energy transmissive window; said control system comprising:
   (a) a laser generator for creating a beam of laser radiation within a certain first predetermined output power level and at a certain first predetermined wavelength;
   (b) a radiant energy transmissive window consisting essentially of a body transmissive to incident radiation within said first predetermined output power level and being arranged to transmit laser beam radiation across the thickness thereof;

(c) an optical transmitting fiber arranged to receive laser generated radiation from said laser generator at the proximal end thereof and to transmit such radiation along the fiber length for delivery into said radiant energy transmissive window, said optical transmitting fiber having a distal tip end disposed adjacent one surface of said radiant energy transmissive window;

(d) a radiant energy transmissive window retention sleeve within said radiant energy discharge assembly for receiving and retaining said optically transmitting fiber adjacent the fiber distal tip and for maintaining said fiber distal tip end in a predetermined position relative to the surface of said radiant energy transmissive window;

(e) said radiant energy transmissive window being adapted to emit fluorescent radiation within a certain second predetermined wavelength upon exposure to radiation from said laser generator and with the strength of said emitted fluorescent radiation being at least in part indicative of the intensity level of incident laser beam energy, and with said second predetermined wavelength being significantly different from said first predetermined wavelength; and (f) sensing means operatively associated with said optical transmitting fiber for detecting the radiation emitted from said radiant energy discharge assembly.

13. The control system of claim 12 wherein:
the strength of said emitted fluorescent radiation is a function of the intensity level of said incident laser beam energy and the temperature of said radiant energy transmissive window.

14. The control system of claim 1 wherein:
the strength of said fluorescent radiation is a function of said power level of said beam of laser energy and the temperature of said lens means.

* * * * *